United States Patent [19]

Peters

[11] Patent Number: 5,366,439

[45] Date of Patent: Nov. 22, 1994

[54] ANKLE BRACE WITH BUBBLE CUSHIONING

[75] Inventor: Rick E. Peters, Louisville, Ky.

[73] Assignee: Active Ankle Systems, Inc., Louisville, Ky.

[21] Appl. No.: 906,574

[22] Filed: Jun. 30, 1992

Related U.S. Application Data

[63] Continuation-in-part of Ser. No. 653,667, Feb. 8, 1991, abandoned, which is a continuation-in-part of Ser. No. 404,125, Sep. 7, 1989, Pat. No. 5,031,607.

[51] Int. Cl.⁵ .............................................. A61F 5/00
[52] U.S. Cl. ......................... 602/27; 602/13; 602/23
[58] Field of Search ........ 128/379, 381, 382, DIG. 20, 128/877; 602/5, 13, 20, 23, 27; 607/108, 109, 111, 112

[56] References Cited

U.S. PATENT DOCUMENTS

| 15,446 | 9/1822 | Hamilton . | |
|---|---|---|---|
| 112,952 | 3/1871 | Niswauder . | |
| 130,639 | 8/1872 | Howe . | |
| 297,688 | 9/1888 | Womack . | |
| 830,894 | 9/1906 | Garrod . | |
| 3,506,000 | 4/1970 | Baker . | |
| 3,674,025 | 7/1972 | Mann . | |
| 3,850,167 | 11/1974 | Seeley . | |
| 3,955,565 | 5/1976 | Johnson, Jr. . | |
| 4,043,330 | 8/1977 | Bansal | 128/877 |
| 4,133,311 | 1/1979 | Karczewski . | |
| 4,166,460 | 9/1979 | Applegate . | |
| 4,280,488 | 7/1981 | Palsky . | |
| 4,280,489 | 7/1981 | Johnson, Jr. . | |
| 4,287,920 | 9/1981 | Johnson, Jr. . | |
| 4,320,748 | 3/1982 | Racette . | |
| 4,378,793 | 4/1983 | Mauldin et al. . | |
| 4,409,976 | 10/1983 | Pence . | |
| 4,433,682 | 2/1984 | Badra . | |
| 4,510,927 | 4/1985 | Peters . | |
| 4,556,654 | 12/1985 | Paulseth . | |
| 4,577,419 | 3/1986 | Chassaing . | |
| 4,590,932 | 5/1986 | Wilkerson . | |
| 4,597,962 | 8/1986 | Greene . | |
| 4,628,945 | 12/1986 | Johnson, Jr. . | |
| 4,665,904 | 5/1987 | Lerman . | |
| 4,693,239 | 9/1987 | Clover, Jr. . | |
| 4,744,351 | 5/1988 | Grundei et al. | 602/19 |
| 4,788,972 | 12/1988 | DeBusk | 602/5 |
| 4,844,094 | 7/1989 | Grim . | |
| 4,865,023 | 9/1989 | Craythorne et al. . | |
| 4,885,811 | 12/1989 | Hayes | 602/13 X |
| 5,007,416 | 4/1991 | Burns et al. . | |
| 5,016,623 | 5/1991 | Krahenbuhl . | |
| 5,027,801 | 7/1991 | Grim . | |
| 5,031,607 | 7/1991 | Peters . | |

OTHER PUBLICATIONS

European Patent Office, German applications, Gyory (0048442) w English translation of pp. 8–12.

Primary Examiner—Richard J. Apley
Assistant Examiner—Linda C. M. Dvorak
Attorney, Agent, or Firm—Middleton & Reutlinger

[57] ABSTRACT

An ankle brace for protecting and exercising an injured ankle includes a heel portion, inner and outer pivot legs, and padding which lies between the wearer's leg and the brace.

5 Claims, 7 Drawing Sheets

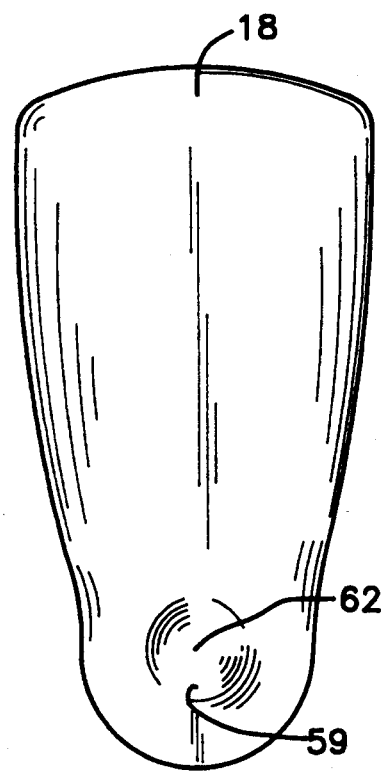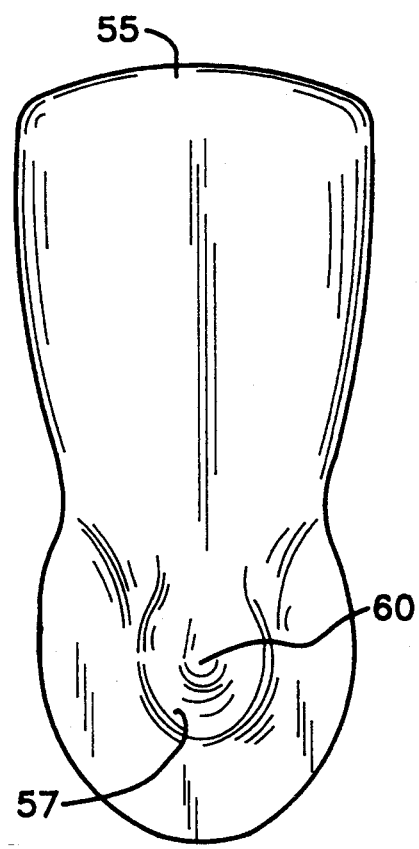
FIG. 10
FIG. 11

ANKLE BRACE WITH BUBBLE CUSHIONING

This application is a continuation-in-part of U.S. patent application Ser. No. 07,653,667 filed on Feb. 8, 1991, now abandoned, which is a continuation-in-part of U.S. patent application Ser. No. 07,404,125, filed on Sep. 7, 1989 and issued as U.S. Pat. No. 5,031,607 on Jul. 16, 1991, entitled "Ankle Brace" by Rick E. Peters.

BACKGROUND OF THE INVENTION

The present invention relates to ankle braces, and, in particular, to an ankle brace which permits flexing of the ankle forward and backward (plantarflexion and dorsiflexion) while preventing the ankle from flexing inward or outward (inversion or eversion), in order to promote healing of an injured ankle or prevent injury to an injury-prone ankle during exercise.

Ankle injuries are among the most common injuries in sports. In order to protect the ankle, many athletes have wrapped the ankle area with adhesive tape. The application of tape is expensive both because it is time consuming and because of the cost of the tape itself. It is also not very effective, because the tape loosens quickly after exercise is begun. The use of tape has also been shown to weaken ankles if used over a long period of time because it causes a loss of plantarflexion and dorsiflexion.

When an ankle is injured, the traditional method for promoting healing is to apply pressure to the area to reduce swelling. The current method for applying pressure is to apply it over a large area, which limits the range of motion of the ankle. When large areas are covered by a compression device, the material contacting the foot must be fairly flexible or soft, such as an elastic bandage or an air bag, in order to avoid being uncomfortable. This severely limits the amount of pressure that can be applied to the injury site to reduce swelling. Also, with an air bag, the foot rubs against the bag in order to move, causing irritation to the foot, and generating heat. It is not desirable to add heat to a swollen ankle.

Another treatment method is to exercise the joint to promote healing. Exercise brings greater blood flow to the area and prevents the atrophy of muscles. The current trend in medicine is to promote exercise as soon as possible. However, in traditional treatment methods, the ankle could not be properly exercised until after the compression was removed, thereby greatly delaying the exercise therapy.

SUMMARY OF THE INVENTION

The present invention provides a reusable ankle brace which closely conforms anatomically to the ankle so that it is comfortable and so that it pivots along the same axis as the ankle.

The present invention provides the greatest possible flexing of the ankle forward and backward (plantarflexion and dorsiflexion) while preventing inversion and eversion of the ankle in order to promote healing.

In addition, the present invention provides an ankle brace with interchangeable pads, so that a thick and relatively stiff compression pad can be used to provide uniform pressure directly on the injured area shortly after it is injured, and, when the swelling is reduced, a thinner exercise pad or bubble cushion pad can be inserted to permit greater freedom of movement.

The compression pad of the present invention covers much less of the foot than other devices, concentrating its compressive force in the area of the injury and leaving the rest of the foot free to move. This means that there is more freedom of movement in plantarflexion and dorsiflexion with the present invention. Plantarflexion and dorsiflexion do not usually cause injury, so this kind of motion is desirable in order to promote healing and reduce muscle atrophy.

The fact that the compression pad of the present invention concentrates its compressive force in the area of the injury also means that this compression pad can be relatively rigid and therefore apply more pressure to the injured area without being uncomfortable.

The use of the ankle brace of the present invention provides the optimum combination of pressure applied to the injured area to reduce swelling and flexibility of the joint to permit exercise which promotes healing and reduces muscle atrophy. In this way, a single brace provides the benefits both of a compression strategy and an exercise strategy to promote healing, while protecting the ankle from further injury.

The ankle brace of the present invention also gives the wearer control over the treatment of the injury, which permits the treatment to be quickly changed, depending on the condition of the ankle.

The present invention provides a rear, angular strap which improves the function of the brace. It eliminates any problem with the brace sliding forward on the foot while, at the same time, providing a better fit and additional stability to prevent inversion. Since inversion injuries are about 85% of the ankle injuries, this additional support is very helpful.

The present invention also provides a single D-ring pivotally connected external to the lateral side of the outer pivot strap and located below the ankle joint. The D-ring is designed to pivot with respect to the vertical axis to accommodate either a left or right ankle by simply turning the ankle brace around and pivoting the D-ring to the anterior or frontal position opposite the pivot strap. The D-ring is provided to receive one lateral shoe lace from the wearer's shoe and to provide a means to prevent additional rotational stress on the wearer's ankle.

In one embodiment, the invention includes a cold pack insert, which can be used shortly after injury to reduce swelling. The cold pack may also be used periodically as needed, such as to prevent swelling after exercise.

Another embodiment utilizes a bubble cushion pad which incorporates at least one multi-layer bubble pad comprising non-porous pressurized bubbles enclosed within a sealable envelope that provide a constant bubble barrier between the ankle and the outer plastic shell which provides structural support. Although the use of vinyl envelopes and the use of air bubbles for cushioning are known in the art, the novel multi-layer bubble pad in a sealable envelope has not been utilized as a cushioning means for ankle supports heretobefore.

The bubble cushion pads taught in the prior art use bubble material having a top layer of film formed having bubble caps extending outwardly therefrom, being sealed with a second layer of film adhering to the first layer to seal air within the bubble. The two ply bubble material shown in the prior art is not effective in a high stress area, such as an ankle brace, because of the constant breaking of the bubbles while under stress. Other types of conventional pads having an air bubble support which utilize an air filled envelope forming a single air pocket or a porous foam filler have no means to restrict the movement of the air within the pocket, and are therefore ineffective in providing structural support and uniform compression to the injured area.

The numerous non-porous pressurized bubbles throughout the multi-layer bubble pad enclosed within the vinyl envelope of the present invention distribute the pressure evenly so that it is placed over the entire ankle. Other types of devices that use a porous filler pad, place the entire pressure over the most prominent point on the ankle, which in most cases is the most painful area. In other devices that use a porous foam filler with a vinyl covering, puncturing the covering allows the air entrapped inside the porous foam to escape which renders the pad useless for cushioning the ankle against the hard outer plastic shell. These foam or porous pads used as a cushioning means tend to bottom out and thus produce a painful irritation to the malleolus.

The multi-layer bubble pads used in the bubble cushion pads of the present invention have been designed as a barrier which will prevent the malleolus from bottoming out against the hard plastic shell as does the air bubble and foam types of pads currently in use. The pressurized non-porous soft bubbles of the bubble cushion pad are surrounded by a vinyl envelope. If the vinyl envelope is punctured, the individual pressurized bubbles will still provide the necessary cushioning effect.

The bubble cushion pad provides a softer barrier and more uniform compression around the ankle than gel filled packs or foam filled envelopes. The use of a gel pack is known throughout the industry as providing too much weight to the ankle brace. The extra weight of the gel packs inhibits their use as a preventive injury ankle support by athletes concerned with agility and speed, the use of heavy gel pads in an ankle support is painful to the wearer having an ankle injury.

The bubble cushion pad provides stability to the ankle when inverting (turning in) or everting (turning out) of the ankle occurs. The non-porous pressurized bubbles provide the necessary cushioning effect, while providing a constant, or static filler between the ankle and the ankle brace, thus increasing the stability of the ankle support when stress is increased due to turning of the ankle. With a porous pad filler, turning of the ankle causes air to escape from the point of the pad with the most pressure from the outer plastic shell. This causes pain to the bottomed out area of the ankle and dispersion of the air to other parts of the pad disrupting the stability of the ankle brace, and contributing to the forces that are turning the ankle in the direction of the injury.

The bubble cushion pad is interchangeable with the non-porous neoprene exercise and compression pads. Aligned adjacent the top of the ankle brace, the bubble cushion pad may cover as much as the full length of the ankle brace. Other non-hinged ankle braces have cushioning that cover the full length of the ankle brace irritate the bottom of the ankle whenever ankle joint movement occurs. The bubble cushion pad will not inhibit the forward and backward (plantarflexion and dorsiflexion) flexing motion of the ankle. Research indicates that other types of cushioning means which cover the full length of the ankle support device tend to restrict plantarflexion and dorsiflexion motion.

The present ankle brace is also designed so that it provides the same excellent fit on either the left or right foot, thereby reducing the number of braces that need to be kept in stock in a doctor's or trainer's office while overcoming the problems of box-like, symmetrical braces which do not provide good fit.

BRIEF DESCRIPTION OF THE DRAWINGS

FIG. 10 is a side view showing the inside of one of the exercise pads shown in FIG. 1; and FIG. 11 is a side view showing the inside of the compression pad shown in FIG. 2.

DESCRIPTION OF THE PREFERRED EMBODIMENTS

Figure 1:
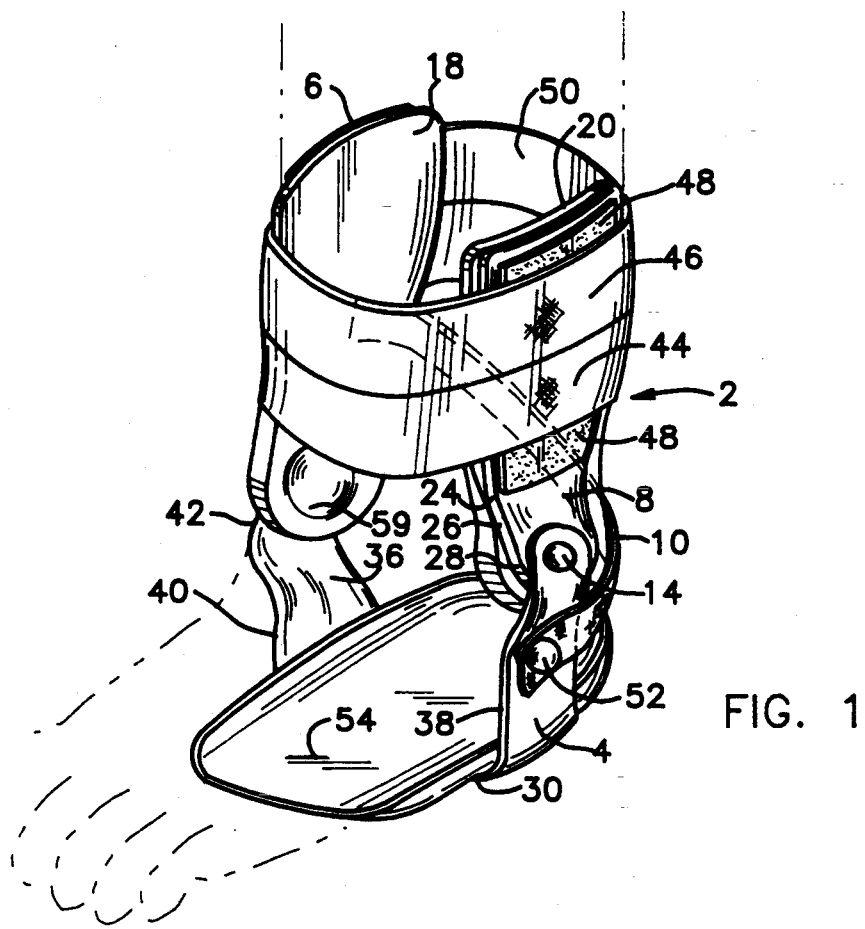
FIG. 1 is a perspective view taken from the front left side of an ankle brace made in accordance with the present invention, including two exercise pads, and showing the left foot.

The present invention is an ankle brace 2 which includes a heel stirrup 4, to which are attached an inner pivot leg 6, an outer pivot leg 8, and a pivot strap 10. Rivets 12 and 14 connect the inner pivot leg 6 and outer pivot leg 8, respectively, to the heel stirrup 4. The outer rivet 14 preferably is positioned slightly lower than the inner rivet 12 to correspond with the outer and inner pivot points of the ankle bones (the lateral malleolus and medial malleolus, respectively). This can be seen most clearly in FIG. 4, in which the distance "a" from the outer rivet 14 to the flat bottom 30 of the heel stirrup 4 is less than the distance "b" from the inner rivet 12 to the flat bottom 30. Thus, the ankle brace pivots along the same axis as the foot, providing maximum comfort and maximum flexing of the ankle forward and backward (plantarflexion and dorsiflexion). The heel stirrup 4 and the pivot legs 6, 8 are made of a relatively stiff material, such as polypropylene, and they overlap substantially in the vertical direction, so as to severely limit flexing inward or outward (inversion or eversion). Inward and outward flexing could re-injure the ankle and therefore must be prevented while still permitting as much flexibility of the ankle as possible.

Figure 3:
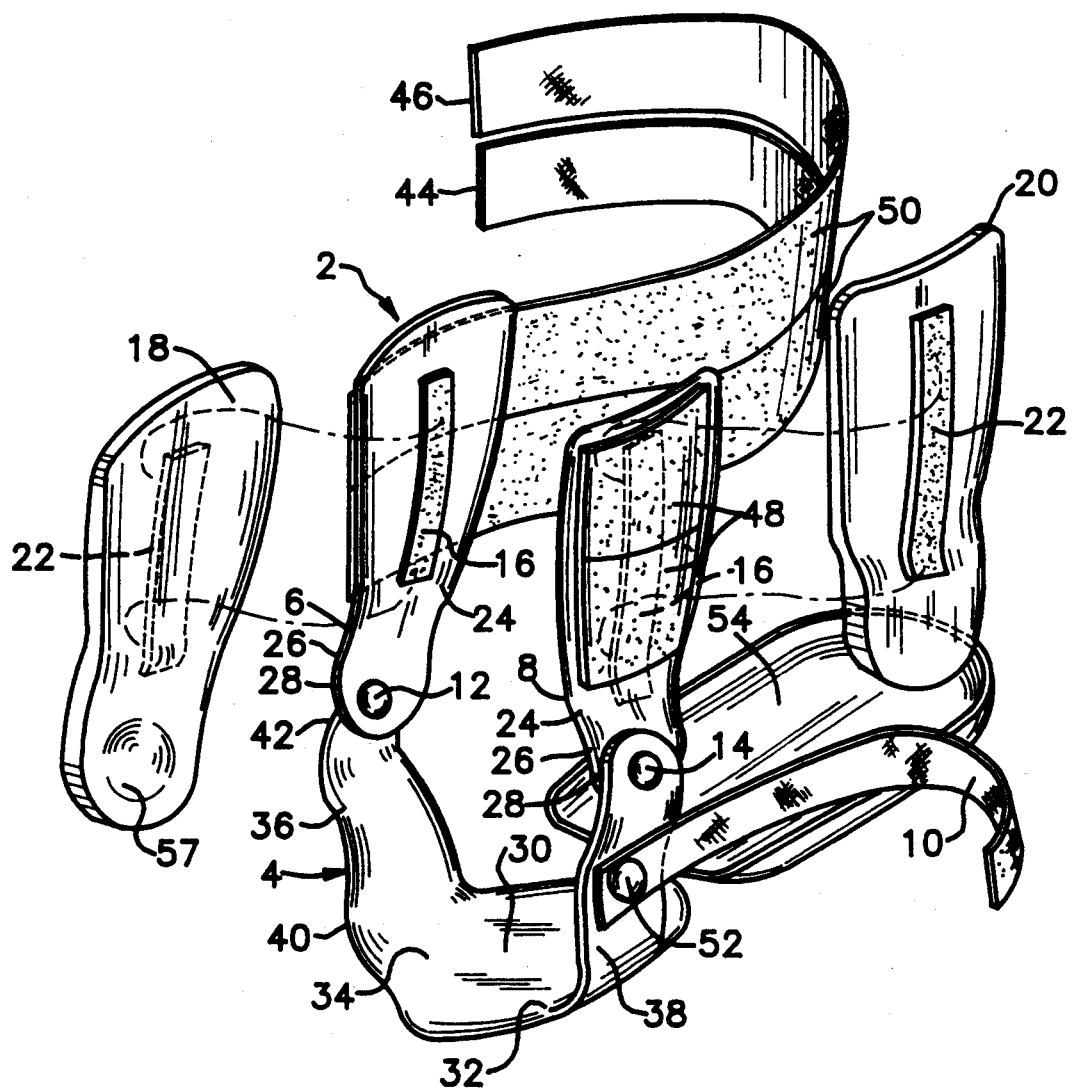
FIG. 3 is an exploded perspective view of the ankle brace of FIG. 1.
Figure 4:
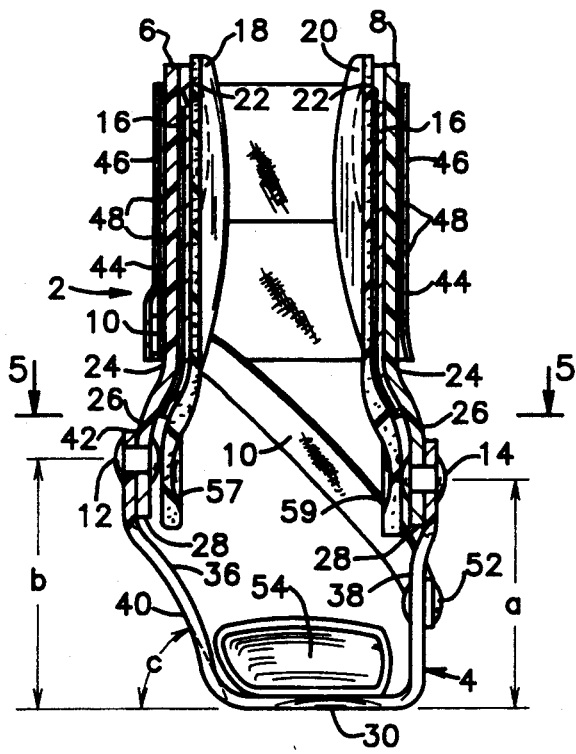
FIG. 4 is a front view of the ankle brace of FIG. 1.
Figure 6:
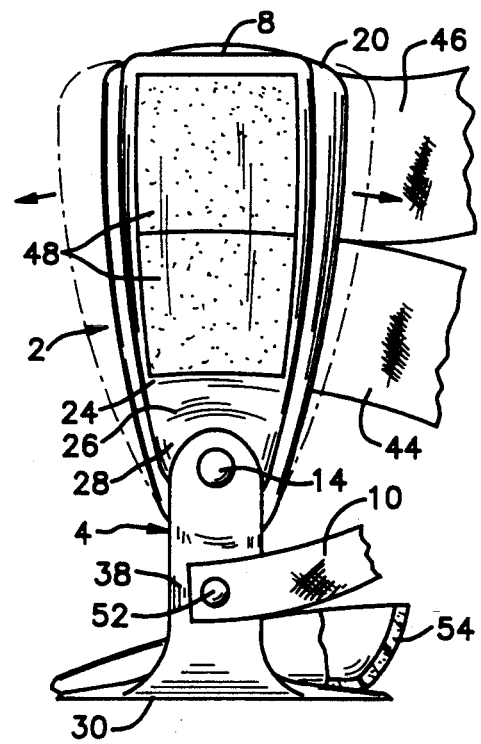
FIG. 6 is a side view of the ankle brace of FIG. 4, with different positions shown in phantom.

On the inside of the pivot legs 6, 8 are releasable attachment means 16. In this embodiment, strips of material including the hook side of a hook and loop type of connector such as the Velcro TM brand are glued to the pivot legs at the points 16. As shown in FIGS. 1, 3 and 4, inner and outer exercise pads 18, 20 are mounted on the inside of the inner and outer pivot legs 6, 8, respectively. Each exercise pad 18, 20 has a strip of loop connector material 22 glued to its outer surface. This strip 22 mates with the corresponding strip 16 on the inside of the pivot legs 6, 8. This permits the pads 18, 20 to be easily attached to and removed from the ankle brace 2. This method of attachment also permits the pads 18, 20 to be adjusted up, down, forward, or rearward to fit the wearer.

The inner and outer pivot legs 6, 8 are contoured at the top to wrap partway around the side of the wearer's leg. This contour provides good surface area contact between the brace and the wearer's leg, which makes the brace comfortable and effective. The contour also prevents the pivot legs 6, 8 from sliding forward or backward on the wearer's leg. The contour also permits a comfortable fit for a variety of sizes of wearers' legs.

The lower one-third of each of the pivot legs 6, 8 bends outward in the area 24 and then downward in the area 26. This imitates the shape of the inner and outer ankle bones, thereby providing maximum surface area contact in the area of the ankle which needs support. This makes the brace more comfortable and more effective than if the pivot legs 6, 8 were straight. It is also makes the brace smaller so it can fit into the wearer's shoe more readily. The lowermost portion 28 of the pivot legs (through which the rivets 12, 14 pass) lies in a vertical plane (perpendicular to the flat bottom 30 of the heel stirrup 4) to encourage the forward and backward flexing of the foot while restricting inward and outward flexing.

Figure 5:
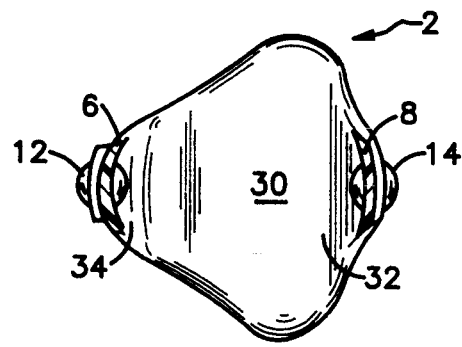
FIG. 5 is a view taken along the section 5—5 of FIG. 4, with the heel pad removed.

The heel stirrup 4 fits inside the wearer's shoe, and the bottom 30 lies under the wearer's heel. As shown in FIG. 5, the flat bottom 30 is considerably longer in the region 32 which lies below the outer pivot leg 8 than in the region 34, which lies below the inner pivot leg 6. The long area 32 provides a large support base for the outer portion of the foot, and the tapering of the bottom 30 to the shorter region 34 provides greater comfort in the arch area of the foot. While the brace is not symmetrical, it can be turned around and used on the other foot to provide the same excellent fit on either foot. This greatly reduces the inventory that a trainer or doctor would have to maintain.

The heel stirrup 4 is substantially U-shaped, with the flat bottom 30 connecting inner and outer upright portions 36, 38, respectively. The outer upright 38 extends substantially vertically from the flat bottom 30 for approximately one-third of its height, then bends outward slightly, and then returns to a substantially vertical direction in the portion through which the rivet 14 passes.

The inner upright 36 extends away from the base 30 at an angle C (shown in FIG. 4) of approximately seventy-five degrees. This angled portion 40 extends for approximately two-thirds of the height of the inner upright 36. This angle corresponds anatomically with the shape of the inside of the ankle when it is bearing weight. When the foot bears weight, the inside of the foot flattens and rolls slightly inward. The upper one-third portion 42 of the inner upright 36 extends vertically, putting it in line with the ankle bone. As was explained earlier, the outside rivet 14 defines a pivot point which is lower than the pivot point defined by the inside rivet 12. In other words, the outside pivot point 14 is located a shorter vertical distance from the flat bottom 30 of the stirrup than is the inside pivot point 12.

Two connecting straps 44, 46 are attached to the upper portion of the pivot legs 6, 8 to keep the pivot legs 6, 8 close to the user's leg. These straps 44, 46 preferably have a loop connector material on their inside surface 50, and the mating hook connector material is located in strips 48 glued to the outside of the pivot legs 6, 8. The outside surface of the straps 44, 46 may also include some of the hook connector material so that the straps 44, 46 can be securely wrapped onto themselves.

The pivot strap 10 is pivotally mounted on the lower straight portion of the outer upright 38 by means of a rivet 52. This means that the pivot strap 10 is riveted below the point at which the outer pivot leg 8 pivots relative to the stirrup 4. The pivot strap 10 crosses behind the wearer's leg and attaches to the hook connector strip 48 on the outside of the inner pivot leg 6. In this way, the strap 10 prevents the brace 2 from sliding forward relative to the user's foot. The angle of the strap 10 also provides force in the proper direction to hold the outer upright 38 close to the ankle and to prevent any increase in the angle between the inner upright 36 and the flat bottom 30 (which would be a decrease in the angle C of FIG. 4), thereby providing a force which opposes any inversion of the ankle. When the ankle brace 2 is turned around and used on the right foot (not shown), the pivot strap 10 simply pivots so that it will cross the other side of the brace (formerly the front side, which will then be the back).

Figure 15:
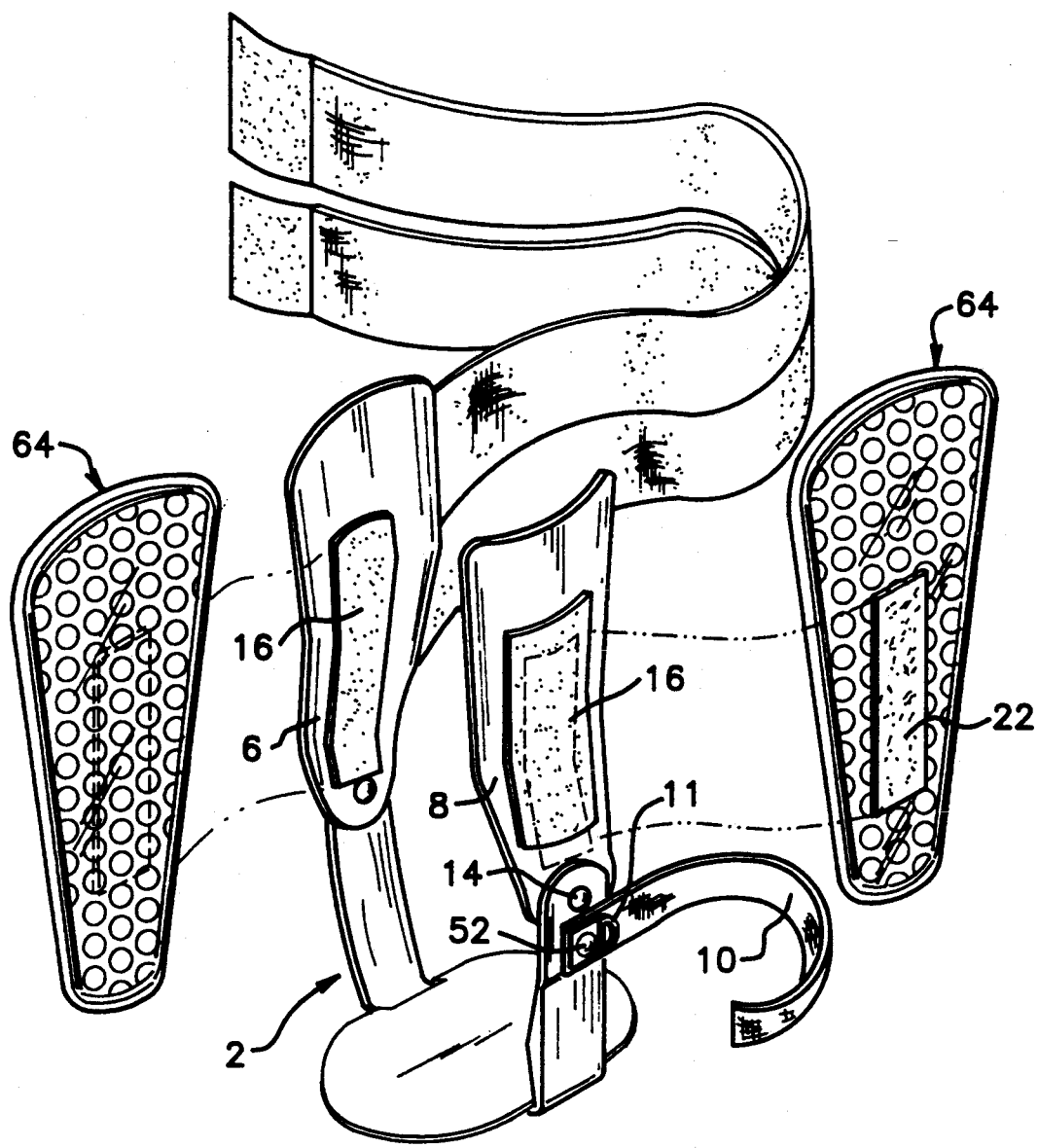
FIG. 15 is an exploded perspective view of the ankle brace of FIG. 1 incorporating a pair of bubble cushion pads.

As shown in FIG. 15, a single D-ring 11 is pivotally connected external to the lateral side of the outer pivot strap 10 by a rivet 52. The D-ring 11 is positioned between the pivot strap 10 and the head of the rivet 52 located below the ankle joint outside pivot point rivet 14 on the outer pivot leg 8. The D-ring 11 is designed to pivot with respect to the vertical axis to accommodate either a left or right ankle by simply turning the ankle brace 2 around and pivoting the D-ring 11 to the anterior or frontal position opposite the pivot strap 10. The D-ring 11 receives one lateral shoe lace from the wearer's shoe and provides a means to prevent additional rotational stress on the wearer's ankle.

The D-ring 11 increases inversion protection in two ways. Incorporating the lateral shoe lace through the D-ring 11 prevents posterior movement of the lateral or outside pivot leg 8 and anterior movement of the medial or inside pivot leg 6, thereby preventing migration of the ankle brace and maintaining it in its original applied position which results in increased stability.

Holding the outside pivot leg 8 closer to the ankle provides more effective treatment to the injury. For when inversion occurs, an ankle brace has a tendency to migrate anteriorly on the medial side, thus making the ankle brace unstable. Providing a D-ring 11 on the medial side would promote undesired anterior migration and limit the effectiveness of the D-ring 11 on the lateral side. Applicants research has revealed that approximately 85% of ankle sprains are of the inversion type. Therefore, positioning the D-ring 11 on the lateral side provides the most effective treatment.

A heel pad 54 may be placed on top of the flat bottom 30 to receive the wearer's heel. The heel pad 54 is preferably made of a soft material which will cushion the wearer's heel.

Figure 2:
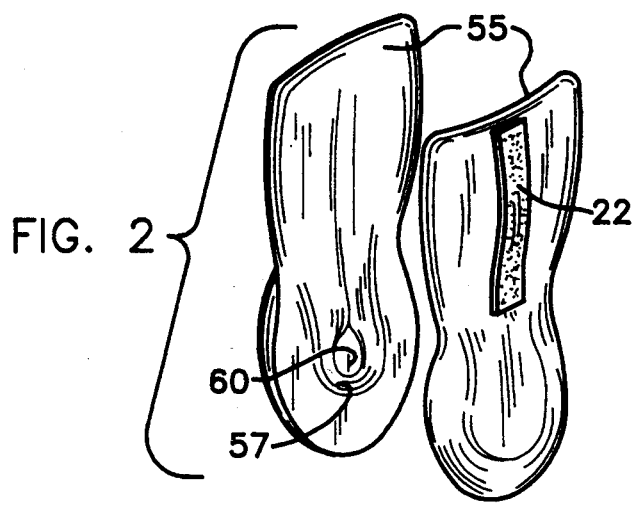
FIG. 2 is a perspective view of two compression pads made in accordance with the present invention.
Figure 7:
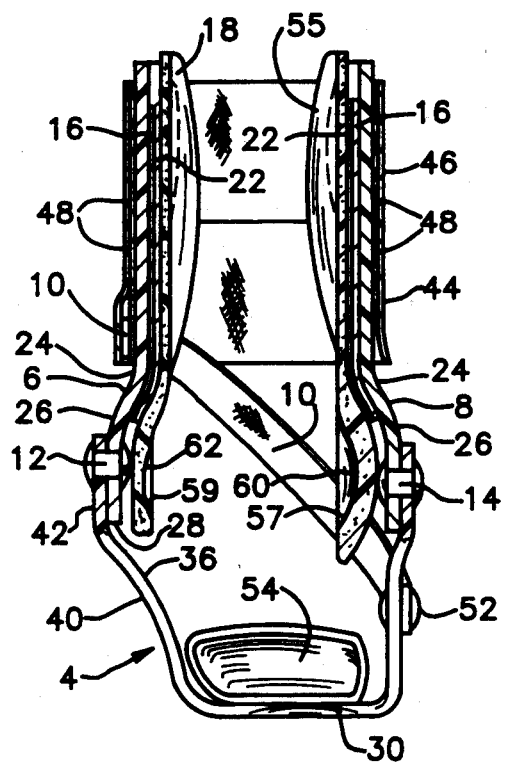
FIG. 7 is a front view of the ankle brace of FIG. 1 except that the outer exercise pad has been replaced by one of the compression pads shown in FIG. 2.

A compression pad 55, as shown in FIGS. 2, 7, and 11 can be used to replace the exercise pad 18 or 20, when edema or swelling are present. The compression pad 55 will usually be worn only on the side of the foot that is injured, usually the outside, as shown in FIG. 7, leaving an exercise pad 20 or 18 on the other side. The compression pad 55 is made of a stiffer material than the exercise pad. In the preferred embodiment, both the exercise pads and the compression pads are made of urethane foam, and the compression pad is denser, making it stiffer. The compression pad is wider and thicker than the exercise pad in the area of the ankle and has a deep, rounded indentation 57 which cups around the ankle bone to provide localized pressure on the injury site.

As shown in FIG. 7, the deepest part 60 of the indentation 57 is aligned with the center of the rivet 14, which defines the pivot point. The exercise pad 18 also has an indentation 59 to receive the ankle bone, but that indentation 59 is much shallower than the indentation 57 of the compression pad 55. The deepest part 62 of the indentation 59 in the exercise pad 18 is also aligned with the pivot point of its respective side of the brace, but it should be noted that the compression pad extends a substantially greater distance downward from the deepest part 60 of its indentation 57 than does the exercise pad. This is necessary in order for the compression pad 55 to apply pressure completely around the bone on the side of the ankle that is injured. If the injury were on the inside of the ankle, the compression pad 55 and exercise pad 18 of FIG. 7 would switch sides, with each pad's indentation aligned with the pivot point of its respective side.

The compression pad 55 is curved or contoured in its upper two-thirds to help fit around the leg. As with the exercise pads 18, 20, the compression pad 55 has a loop connector portion 22 on its outer surface which mates with the hook connector portion 16 on the inside of the pivot leg. This form of attachment permits the compression pad to be adjusted relative to the pivot leg 6 or 8 for the best fit. The compression pad 55 thereby fits precisely around the injured ankle to apply pressure directly on the injury. This prevents the compression pad 55 from sliding forward or backward on the user's leg and permits greater pressure to be applied to the injury comfortably, without restricting movement any more than necessary. The compression provided by the compression pad 55 will reduce edema or swelling that may normally follow an injury or exercise. Reducing this swelling decreases the severity of the injury, shortens recovery time, decreases pain, and increases the range of motion of the joint.

The interchangeability of the exercise pad, bubble pad, and the compression pad allows the wearer to control his own treatment, permitting him to use a compression pad when swelling is a problem and then to switch to the exercise pad as soon as the swelling goes down. This maximizes the benefits from both the compression and the exercise types of therapy.

Figure 8:
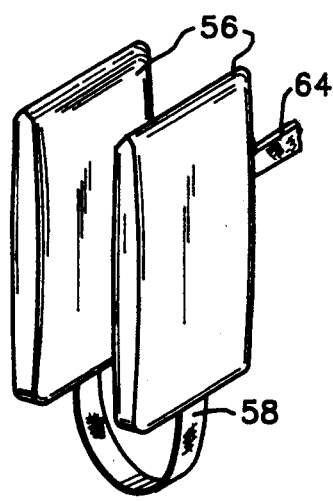
FIG. 8 is a perspective view of a pair of cold packs.
Figure 9:
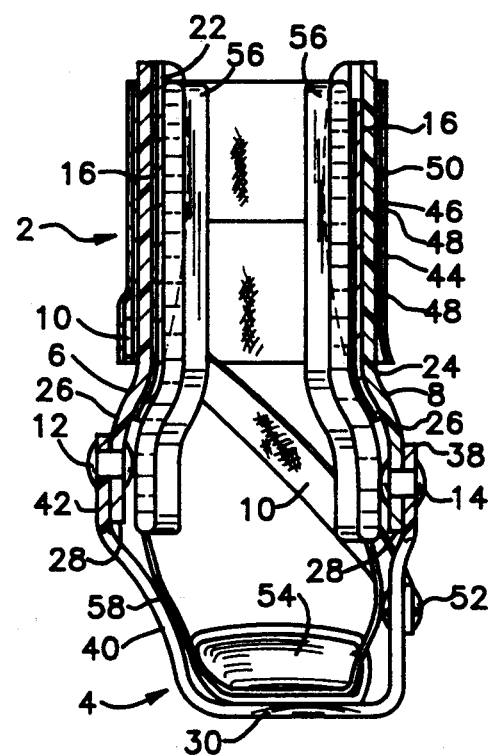
FIG. 9 is a front view of the device shown in FIG. 1 except that cold packs are replacing the exercise pads.

A pair of fluid-filled packs 56, as shown in FIGS. 8 and 9, can also be used in the present invention. The fluid-filled packs 56 have an outer surface made of a material which will stick to the hook fasteners. The two fluid-filled packs are joined by a strap 58 which passes under the foot, and another strap 64 may be used to wrap around the two fluid-filled packs to secure them to the wearer's leg. The fluid-filled packs are chilled by placing them in a freezer, and then they are attached to the inside of the pivot legs 6, 8 by means of the hook connectors on the legs 6, 8 and the mating fabric cover on the packs 56. The fluid-filled packs 56 chill the area of the injury, thereby reducing swelling.

In a typical treatment plan, the chilled packs 56 are applied immediately after injury for about twenty minutes. Then, the cold packs 56 are removed, a compression pad 55 is inserted into the brace on the side of the injury, and an exercise pad 18 or 20 is inserted on the other side. The injured person uses this arrangement of the brace until the swelling goes down. Then the compression pad 55 is removed, and another exercise pads 18 or 20 is used to replace the compression pad 55.

A bubble cushion pad 64 as shown in FIGS. 12-15 can also be used interchangeably with the exercise pad 18 or the compression pad 55, when pain and soreness are evident around the ankle. The bubble cushion pad 64 can be worn on one or both sides of the ankle as shown in FIG. 15. The bubble cushion pad 64 is durable, provides uniform compression, and is a softer more forgiving pad for use with the recently injured ankle. The thinness of the bubble cushion pad 64 permits the ankle brace 2 to be held closer to the skin of the wearer providing a more effective brace and ankle support. The non-porous air bubble cushion pad 64 provides a light-weight air bubble barrier between the sore ankle and the outer plastic shell. Also, the air bubble cushion pad 64 provides an excellent support for preventing injury to the ankle and its light weight, thinness, and non-heat absorbing features provide an excellent ankle support for athletes prone to ankle injury and is preferable to thick, bulky, and heavy pads currently being used as preventive supports.

Figure 12:
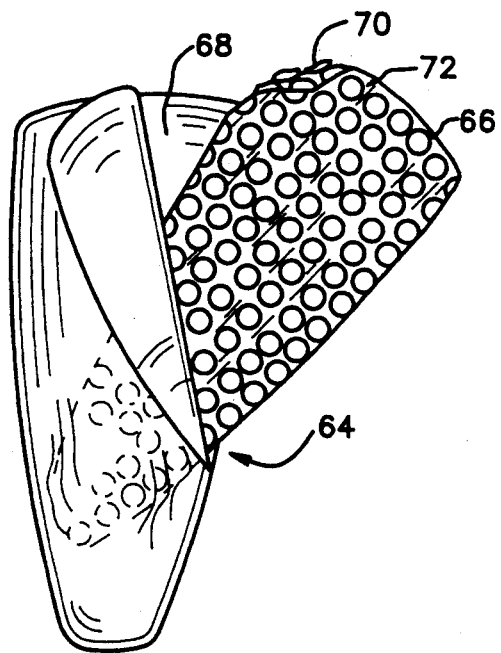
FIG. 12 is a perspective view showing a bubble cushion pad having a single multi-layer bubble pad partially enclosed within a sealable vinyl envelope.
Figure 13:
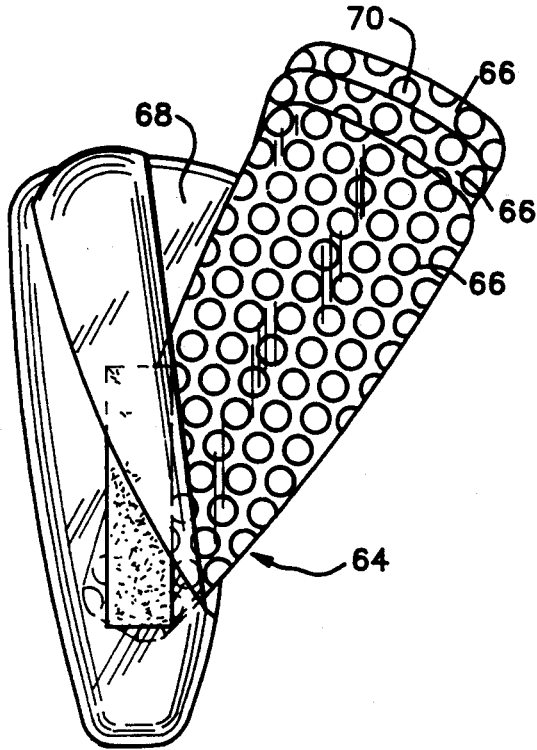
FIG. 13 is a perspective view showing a bubble cushion pad containing a plurality of multi-layer bubble pads partially enclosed within a sealable vinyl envelope.
Figure 14:
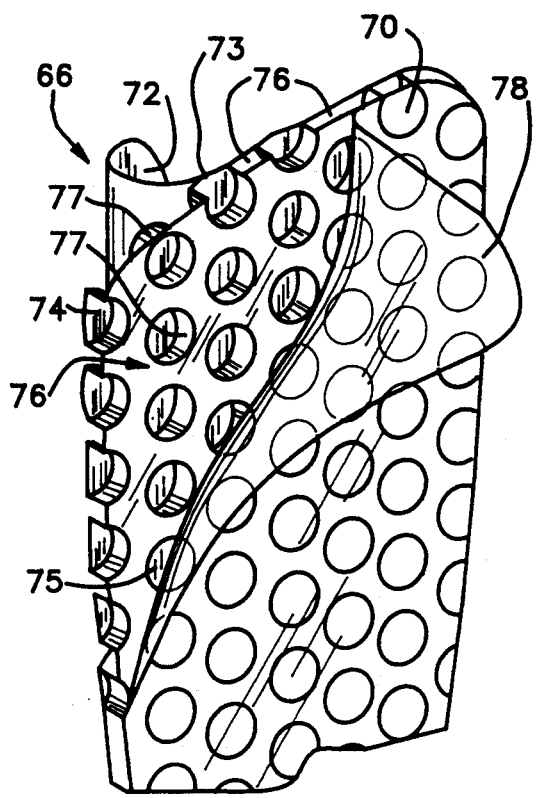
FIG. 14 is a perspective view of the bubble pads of FIGS. 12 and 13 showing the multi-layer construction of the pad, and showing an outer first film adhering to the top surface of the bubble caps extending outward and formed within an intermediate second film and forming an air tight seal within the interstitial area between the first and second films and the walls of the bubble caps, and showing an outer third film adhering to the bottom of the intermediate second film forming an air tight seal at the bubble base.

As illustrated in FIGS. 12-14, the bubble cushion pad 64 has several unique structural features attributed to its design which incorporates a single or plurality of multi-layer bubble pads 66 enclosed within a sealable plastic envelope 68 as an outer protective cover. The sealed plastic envelope 68 provides a means of containing and positioning the bubble pad(s) 66 and provides a cushioning effect when used in combination with the bubble pad(s) 66 so as to provide optimal support to the injured area. Use of the sealable envelope 68 also prevents slippage of the bubble pads 64 after alignment.

The plastic envelope 68 is shown best in FIGS. 12 and 13 and is comprised of a flexible thermoplastic material. The thermoplastic material in the preferred embodiment is vinyl; however, it is contemplated that other thermoplastic polymers such as polyethylene could be used as well.

A bubble cushion pad 64 such as is used in the preferred embodiment is shown in FIG. 13 containing a plurality of multi-layer bubble pads 66 partially enclosed within a sealable vinyl envelope 68. The bubble pad(s) 66 can also be cut in to pieces or strips and aligned, overlapped, and/or layered within the envelope 68 in such a manner as to provide additional support and protection for a particular area of the wearer's ankle. The plastic envelope 68 may be fabricated having pores or of a mesh construction to be air permeable in addition to providing a means for containing and positioning the bubble pad(s) 66 to provide optimal support to the injured or weakened area of the wearer's ankle. The plastic envelope 68 may also be formed so as to be resealable so that the number of layers or type of bubble pad(s) 66 may be changed depending upon the extent of the injury or to provide the desired structural support for the ankle and to provide maximum cushioning to the injured area.

The bubble pad(s) 66 as shown in FIGS. 12, 13, and 15 incorporate several non-porous pressurized bubbles 70. The bubble cushion pad 64 utilizes one of more multi-layered bubble pads 66 having bubbles of uniform dimensions to effectively concentrate the support and cushioning effect of the bubble cushion pad 64 around the injured area; however, it is contemplated that the bubbles within an individual bubble pad 66 can be formed having various sizes and shapes, such as being generally, oblong, rectangular, oval, donut shaped, triangular, square, etc. so as to provide optimal support for a particular type of ankle injury.

The plastic vinyl envelope 68 of the preferred embodiment is filled with as least one multi-layer bubble pad 66 which is sealed within the envelope 68 so as to form a water and air-tight seal such as shown in FIG. 12. The multi-layer construction of the pad is best shown in FIG. 14. The bubble pad 66 of the preferred embodiment is formed by a coextrusion process which coextrudes three sheets or films of a thermoplastic polymer, such as polyamide polymer, more particularly, nylon, which adhere to one another to form the novel multi-layer bubble pad having unique structural properties. The use of nylon film is particularly adaptable for providing a thin bubble pad 66 which is light weight, flexible, tough, resilient, inexpensive, which forms bubbles 70 which are virtually indestructible and extremely difficult to puncture by the pressure exerted from stress within the ankle support or by mashing the bubbles together with ones hands or fingers. Generally, some type of mechanical means such as a tool or sharp object is needed to puncture the bubbles 70 within the bubble pad 66.

At least three coextruded films comprise the bubble pad 66. The top surface of the bubble pad 66 includes a substantially flat outer first film 72, contiguous with and adhering to the top surface 73 of a bubble cap 74 of each of the bubbles 70 which are formed within and extend outwardly from an intermediate second film 76. Moreover, as shown in FIG. 14, adherence of the outer first film 72 defining the top surface of the bubble pad 66 with the top surface 73 of the bubble caps 74 forms an air tight seal within the interstitial area 76 between the outer first film 72 and the intermediate second film 76 and the walls 77 of the bubble caps 74. The adherence of the first outer film 72 to the top surface 73 of the bubble caps 74 forms a double layer or two ply nylon film on the top surface 73 of the bubble caps 74 and a single ply of film covering the top of the interstitial area 76. The bottom surface of the bubble pad 66 includes a substantially flat outer third film 78 adhering to the flat side of the intermediate second film 76 opposite the bubble caps 74, forming an air tight seal at the base 75 of the bubble cap 74 entrapping air within the bubble 70. Adherence of the outer third film 78 defining the bottom surface of the bubble pad 66 to the intermediate second film 76 forms a single layer of film over the base 75 and between the walls 77 of the bubbles 70, and a two ply layer of film on the bottom of the bubble pad 64 covering the interstitial area 76 between the bubble bases 75.

The bubble cushion pads 64 provide a flexible soft bubble cushion that receives the ankle and provides the necessary softness to decrease pain and soreness to the injured ankle while providing stability to the ankle brace 2. In addition to supporting the injured area of the ankle, the non-porous bubble cushion pad 64 provides a cushion against the pivot legs 6 and/or 8 of the hard plastic shell used for structural support.

As shown in FIG. 15, the bubble cushion pad 64 has a loop connector portion 22 on its outer surface which mates with the hook connector portion 16 on the inside of the inner pivot leg or outer pivot leg 8. This form of attachment permits the bubble cushion pad 64 to be adjusted relative to the pivot leg, 6 or 8, respectively, for the best fit. The bubble cushion pad 64 fits directly on the injury. This permits greater pressure to be applied to the injury comfortably, without restricting movement any more than necessary.

The interchangeability of the exercise pad 18, compression pad 55, and bubble cushion pad 64 allow the wearer to control his or her own treatment, permitting the wearer to use a bubble cushion pad or compression pad when swelling is a problem and then to switch to the exercise pad 18 as soon as the swelling goes down. This maximizes the benefits from both the compression and exercise types of therapy.

The arrangement of the present invention permits a single brace 2 to be used through all the stages of treatment and permits the wearer to control the treatment to minimize pain, protect the ankle, reduce swelling, and exercise the ankle as much as possible to promote healing.

Tests have been conducted comparing the present invention using two exercise pads with other ankle supports on the market, and the results were striking. The range of motion for forward and backward flexing (plantarflexion and dorsiflexion) is substantially greater for the present invention than for conventional supports. The athletes using the present invention were able to apply essentially the same force in plantarflexion as they could without any support, while all other supports reduced the amount of force they could apply. The athletes using the present invention in plantarflexion fatigued at about the same rate as they did without a brace, whereas the users of all other supports exhibited greater fatigue. The present invention also provided substantially greater protection against inversion than all the other supports.

It will be obvious to those skilled in the art that modifications may be made to the embodiments described above without departing from the scope of the present invention.

What is claimed is:

1. An ankle brace to be worn by a wearer to prevent ankle injury or encourage healing of an injured ankle, comprising:
   a heel stirrup, including a bottom portion and inner and outer upright portions;
   inner and outer pivot legs pivotally attached to said inner and outer upright portions at inner and outer pivot points, respectively, wherein the inner pivot point is higher above the bottom portion of the heel stirrup than is the outer pivot point;
   at least one bubble cushion pad adapted to lie between the wearer's leg and said inner pivot leg or said outer pivot leg, said bubble cushion pad defining at least one flexible thermoplastic multi-layer bubble pad containing a plurality of non-porous pressurized bubbles therein;

said bubble pad is of multi-layer construction having an outer first film adhering to the top surface of a plurality of bubble caps extending outward formed within an intermediate second film and forming an air tight seal in the interstitial area between said outer first film, said intermediate second film, and the walls of said bubble caps, and having an outer third film adhering to the bottom of the intermediate second film forming an air tight seal at the base of said bubble cap; and attachment means for adjustably and releasably attaching said bubble cushion pad to its respective pivot leg and adjusting said bubble cushion pad in either the horizontal or vertical axis.

2. An ankle brace to be worn by a wearer to prevent ankle injury or encourage healing of an injured ankle, comprising:

a heel stirrup, including a bottom portion and inner and outer upright portions;

inner and outer pivot legs pivotally attached to said inner and outer upright portions at inner and outer pivot points, respectively, wherein the inner pivot point is higher above the bottom portion of the heel stirrup than is the outer pivot point;

at least one bubble cushion pad adapted to lie between the wearer's leg and said inner pivot leg or said outer pivot leg, said bubble cushion pad defining at least one flexible thermoplastic multi-layer bubble pad containing a plurality of non-porous pressurized bubbles therein;

said bubble pad is of multi-layer construction wherein the top surface of said bubble pad includes a substantially flat outer first film contiguous with and adhering to the top surface of a plurality of bubble caps formed within and extending outwardly from an intermediate second film forming an air tight seal within an interstitial area between said outer first film, said intermediate second film, and the walls of said bubble caps, the adherence of said first outer film to the top surface of said bubble caps forms a multi-ply nylon film on the top surface of said bubble caps and a single ply of film covering the top of said interstitial area, the bottom surface of said bubble pad including a substantially flat outer third film adhering to the flat side of said intermediate second film opposite the top surface of said bubble caps forming an air tight seal between the walls and at the base of said bubble cap entrapping air within so that adherence of said outer third film defining the bottom surface of said bubble pad to said intermediate second film forms a single layer of film over the base and between the walls of the bubbles and forming a two ply layer of film on the bottom of said bubble pad covering said interstitial area between the base of the bubble caps; and attachment means for adjustably and releasably attaching said bubble cushion pad to its respective pivot leg and adjusting said bubble cushion pad in either the horizontal or vertical axis.

3. An ankle brace to be worn by a wearer to prevent ankle injury or encourage healing of an injured ankle, comprising:

a heel stirrup, including a bottom portion and inner and outer upright portions;

inner and outer pivot legs pivotally attached to said inner and outer upright portions at inner and outer pivot points, respectively, wherein the inner pivot point is higher above the bottom portion of the heel stirrup than is the outer pivot point;

at least one bubble cushion pad adapted to lie between the wearer's leg and said inner pivot leg or said outer pivot leg, said bubble cushion pad defining at least one flexible thermoplastic multi-layer bubble pad containing a plurality of non-porous pressurized bubbles therein;

said bubble pad is enclosed within an air permeable means for containing and positioning said bubble pad, wherein said air permeable means is a mesh material; and attachment means for adjustably and releasably attaching said bubble cushion pad to its respective pivot leg and adjusting said bubble cushion pad in either the horizontal or vertical axis.

4. An ankle brace as recited in claim 3, wherein said bubble pad is of multi-layer construction comprising at least three layers of film.

5. An ankle brace to be worn by a wearer to prevent ankle injury or encourage healing of an injured ankle, comprising:

a heel stirrup, including a bottom portion and inner and outer upright portions;

inner and outer pivot legs pivotally attached to said inner and outer upright portions at inner and outer pivot points, respectively, wherein the inner pivot point is higher above the bottom portion of the heel stirrup than is the outer pivot point;

at least one bubble cushion pad and a second bubble pad, exercise pad, or compression pad adapted to lie between the wearer's leg and said inner pivot leg or said outer pivot leg, said bubble cushion pad defining at least one flexible thermoplastic multi-layer bubble pad containing a plurality of non-porous pressurized bubbles therein enclosed within a flexible thermoplastic sealable envelope for positioning said at least one bubble pad and holding said bubble pad securely in position, said bubble cushion pad having an outer first film adhering to the top surface of a plurality of bubble caps extending outward formed within an intermediate second film and forming an air tight seal in the interstitial area between said outer first film, said intermediate second film, and the walls of said bubble caps, and having an outer third film adhering to the bottom of the intermediate second film forming an air tight seal at the base of said bubble cap;

attachment means for adjustably and releasably attaching said bubble cushion pad to it's respective pivot leg and adjusting said bubble cushion pad in either the horizontal or vertical axis, wherein said bubble cushion pad is adapted to be aligned with its respective pivot leg projecting past said pivot point over at least a portion of said inner or outer upright portion of said heel stirrup extending anterior, posterior, superior, and inferior with respect to the wearer's ankle bone to surround and cup the ankle bone in the area around said pivot point, wherein said bubble cushion pad is adjustable in either the vertical or horizontal axis and releasably attachable to said pivot leg;

a pivot strap pivotally connected at one end to the outer upright portion below the outer pivot point, and including pivot strap attachment means for connecting the other end of the pivot strap to the inner pivot leg above the inner pivot point so that the pivot strap lies at an angle to help prevent inversion and said pivot strap is adapted to extend behind the wearer's foot;

a generally flat heel pad adapted to lie on top of the bottom portion of said heel stirrup; and a D-ring pivotally attached external to the lateral side of said outer pivot leg below said outer pivot point and pivotal in the vertical axis for receiving at least one shoe lace from the wearer's shoe for providing a means to prevent additional rotational stress on the wearer's ankle.

* * * * *